US011420916B2

(12) United States Patent
Brennecke et al.

(10) Patent No.: US 11,420,916 B2
(45) Date of Patent: Aug. 23, 2022

(54) SYSTEMS AND METHODS FOR SEPARATION OF OLEFINS FROM MIXTURES THAT CONTAIN REDUCING AGENTS

(71) Applicant: Board of Regents, The University of Texas System, Austin, TX (US)

(72) Inventors: Joan F. Brennecke, Austin, TX (US); Benny D. Freeman, Austin, TX (US); Constanza Miguel Sanchez, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/972,960

(22) PCT Filed: Jun. 10, 2019

(86) PCT No.: PCT/US2019/036277
§ 371 (c)(1),
(2) Date: Dec. 7, 2020

(87) PCT Pub. No.: WO2019/237100
PCT Pub. Date: Dec. 12, 2019

(65) Prior Publication Data
US 2021/0246089 A1 Aug. 12, 2021

Related U.S. Application Data

(60) Provisional application No. 62/682,328, filed on Jun. 8, 2018.

(51) Int. Cl.
*C07C 7/144* (2006.01)
*C07C 5/333* (2006.01)
*B01D 53/22* (2006.01)

(52) U.S. Cl.
CPC ............ *C07C 7/144* (2013.01); *B01D 53/228* (2013.01); *C07C 5/333* (2013.01); *B01D 2053/221* (2013.01)

(58) Field of Classification Search
None
See application file for complete search history.

(56) References Cited

U.S. PATENT DOCUMENTS

| 3,758,603 A | 9/1973 | Steigelmann et al. |
| 4,174,353 A | 11/1979 | Marcinkowsky et al. |

(Continued)

FOREIGN PATENT DOCUMENTS

| EP | 2186784 A2 | 5/2010 |
| WO | 2010033014 A2 | 3/2010 |
| WO | 2011037820 A1 | 3/2011 |

OTHER PUBLICATIONS

International Search Report for International Application No. PCT/US2019/036277 dated Aug. 28, 2019, pp. 1-2.

(Continued)

*Primary Examiner* — Tam M Nguyen
(74) *Attorney, Agent, or Firm* — Meunier Carlin & Curfman LLC

(57) ABSTRACT

The present disclosure pertains to methods and systems for separating olefins from a mixture that includes olefins and non-olefins. The methods include associating the mixture with a support that is embedded with an ionic liquid and a metal ion. The ionic liquid prevents the substantial reduction of the metal ion by reducing agents while the metal ion mediates the transport of the olefin through the support by selectively and reversibly coupling with the olefin. In some embodiments, the support may be in the form of supported ionic liquid porous membranes, and the ionic liquid may be held within the pores of the support by capillary forces. In some embodiments, the support may be in the form of a (Continued)

composite, and the ionic liquid may be dispersed throughout the composite. In some embodiments, the metal ion may be dissolved in the ionic liquid and dispersed throughout the support.

13 Claims, 5 Drawing Sheets

(56) References Cited

U.S. PATENT DOCUMENTS

| | | | |
|---|---|---|---|
| 7,361,800 | B2 | 4/2008 | Herrera et al. |
| 8,778,219 | B2 | 7/2014 | Dai et al. |
| 9,732,016 | B2 | 8/2017 | Ji et al. |
| 2003/0052056 | A1* | 3/2003 | Kim ............... B01D 53/228 210/500.28 |
| 2005/0150383 | A1* | 7/2005 | Kang ............... B01D 53/228 96/11 |
| 2005/0154247 | A1* | 7/2005 | Jong ............... B01D 69/10 585/862 |
| 2006/0016750 | A1 | 1/2006 | Merkel et al. |
| 2006/0264642 | A1 | 11/2006 | Wasserscheid et al. |
| 2007/0213513 | A1* | 9/2007 | Van Alstine ...... C07K 1/22 530/416 |
| 2011/0015461 | A1* | 1/2011 | Dai .................. C10G 31/09 585/818 |
| 2012/0190905 | A1* | 7/2012 | Gorke ............. B01D 53/228 585/818 |
| 2013/0178657 | A1* | 7/2013 | Franke ............. C07C 45/50 568/449 |

OTHER PUBLICATIONS

Written Opinion of the International Searching Authority for International Application No. PCT/US2019/036277 dated Aug. 28, 2019, pp. 1-10.

Aki et al., "High-Pressure Phase Behavior of Carbon Dioxide with Imidazolium-Based Ionic Liquids," The Journal of Physical Chemistry B, vol. 108, 2004, pp. 20355-20356.

Widerhorn et al., "Mechanical Properties: Permeation and Diffusion," Springer Handbook of Materials Measurement Methods, First Edition 2006, Section 7, pp. 283-397, see section 7.6, pp. 371-387.

Tome et al., "Polymeric Ionic Liquid Membranes Containing IL-Ag+ for Ethylene/Ethane Separation Via Olefin-Facilitated Transport," Journal of Materials Chemistry A, vol. 2, 2014, pp. 5631-5639.

Merkel et al., "Silver Salt Facilitated Transport Membranes for Olefin/Paraffin Separations: Carrier Instability and a Novel Regeneration Method," Journal of Membrane Science, vol. 447, 2013, pp. 177-189.

Melody M. Bomgardner, "Output Ramps Up in All Regions," Chemical Engineering News, vol. 89, No. 27, Jul. 4, 2011, pp. 55-63.

Wang et al., "Effect of Hydrogen Reduction of Silver Ions on the Performance and Structure of New Solid Polymer Electrolyte PEI/Pebax2533/AgBF4 Composite Membranes," Materials and Product Engineering, vol. 21, No. 6, 2013, pp. 683-690.

Evanoff, Jr., et al., "Size-Controlled Synthesis of Nanoparticles. 1. "Silver-Only" Aqueous Suspensions via Hydrogen Reduction," J. Phys. Chem. B, vol. 108, 2004, pp. 13948-13956.

Fallanza et al., "Experimental Study of the Separation of Propane/Propylene Mixtures by Supported Ionic Liquid Membranes Containing Ag+-RTILs as Carrier," Separation and Purification Technology, vol. 97, 2012, pp. 83-89.

Kang et al., "Effect of the Polarity of Silver Nanoparticles Induced by Ionic Liquids on Facilitate Transport for the Separation of Propylene/Propane Mixtures," Journal of Membrane Science, vol. 322, 2008, pp. 281-285.

Faiz et al., "Olefin/Parafin Separation Using Membrane Based Facilitated Transport/Chemical Absorption Techniques," Chemical Engineering Science, vol. 73, 2012, pp. 261-284.

Fallanza et al., "Polymer-Ioniic Liquid Composite Membranes for Propane/Propylene Separation by Facilitated Transport," Journal of Membrane Science, vol. 444, 2013, pp. 164-172.

* cited by examiner

SYSTEMS AND METHODS FOR SEPARATION OF OLEFINS FROM MIXTURES THAT CONTAIN REDUCING AGENTS

CROSS-REFERENCE TO RELATED APPLICATIONS

This application claims priority to U.S. Provisional Patent Application No. 62/682,328, filed on Jun. 8, 2018. The entirety of the aforementioned application is incorporated herein by reference.

BACKGROUND

Current systems for separating olefins from non-olefins (e.g., paraffins) have numerous limitations, such as high energy requirements, costly equipment, poor olefin/non-olefin separation properties, poor olefin/non-olefin selectivity, and the need to constantly regenerate and replenish the systems. Various embodiments of the present disclosure address the aforementioned limitations.

SUMMARY

In some embodiments, the present disclosure pertains to methods of separating olefins from a mixture that includes olefins and non-olefins. In some embodiments, the methods of the present disclosure include a step of associating the mixture with a support that is embedded with an ionic liquid and a metal ion. The ionic liquid prevents the substantial reduction of the metal ion by reducing agents while the metal ion mediates the transport of the olefin through the support by selectively and reversibly coupling with the olefin.

In some embodiments, the methods of the present disclosure also include a step of dehydrogenating the mixture prior to associating the mixture with a support. In some embodiments, the dehydrogenation forms olefins from the non-olefins and generates hydrogen gas. As such, in some embodiments, the methods of the present disclosure also include a step of removing at least some of the generated hydrogen gas prior to associating the mixture with the support.

In some embodiments, the mixture is a gaseous mixture. In some embodiments, the mixture includes less than 0.5 wt % of metal ion stabilizing agents, such as hydrogen peroxide and nitric acid.

In some embodiments, the mixture is associated with a support by contacting the mixture with the support. In some embodiments, the support includes, without limitation, porous supports, ceramic-based supports, organic supports, polymer-based supports, metal-based supports, aluminum oxide-based supports, inorganic supports, composites, polymer composites, ionic liquid/polymer composites, membranes thereof, and combinations thereof. In some embodiments, the support includes porous membranes.

In some embodiments, the support is in the form of supported ionic liquid porous membranes. In some embodiments, the ionic liquid is held within pores of the supported ionic liquid porous membranes by capillary forces.

In some embodiments, the support is in the form of a composite, such as a polymer composite. In some embodiments, the ionic liquid is dispersed throughout the composite.

In some embodiments, the ionic liquid includes, without limitation, cations, anions, organic ionic liquids, organic anions, organic cations, inorganic ionic liquids, inorganic cations, inorganic anions, and combinations thereof. In some embodiments, the ionic liquid includes a salt of an organic cation and an anion.

In some embodiments, the ionic liquids include imidazolium-based ionic liquids. In some embodiments, the imidazolium-based ionic liquids include, without limitation, 1-Ethyl-3-methylimidazolium bis(trifluoromethylsulfonyl)imide ([emim][Tf$_2$N]), 1-hexyl-3-methylimidazolium bis(trifluoromethyl sulfonyl)imide ([hmim][Tf$_2$N]), 1-hexyl-2,3-dimethylimidazolium bis(trifluoromethylsulfonyl)imide ionic liquid ([hmmim][Tf$_2$N]), 1-hexyl-3-methylimidazolium trifluoromethanesulfonate ([hmim][TfO]), and combinations thereof.

In some embodiments, the metal ion is dissolved in the ionic liquid and dispersed throughout the support in the form of individual atoms. In some embodiments, the metal ion includes, without limitation, transition metal ions, silver ions, copper ions, nickel ions, iron ions, manganese ions, zinc ions, and combinations thereof. In some embodiments, the metal ions include silver ions.

In some embodiments, the methods of the present disclosure provide an olefin/non-olefin selectivity of at least about 6 at 35° C. In some embodiments, the methods of the present disclosure provide an olefin/non-olefin selectivity of at least about 7 at 35° C.

Additional embodiments of the present disclosure pertain to systems for separating olefins from a mixture that includes olefins and non-olefins. Such systems generally include a support embedded with an ionic liquid and a metal ion such that the ionic liquid prevents the substantial reduction of the metal ion by reducing agents while the metal ion mediates the transport of the olefin through the support by selectively and reversibly coupling with the olefin.

DETAILED DESCRIPTION

Figure 1A:
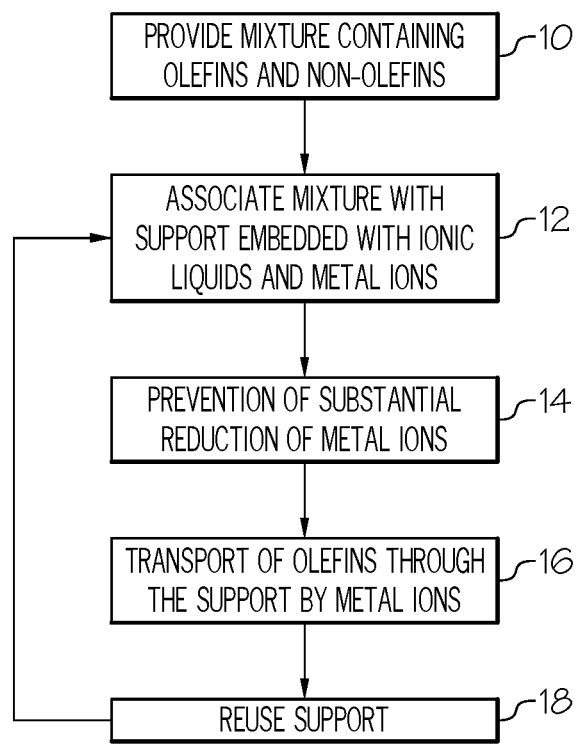
FIG. 1A provides a scheme of a method for separating olefins from a mixture.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Current technologies for separating olefins from non-olefins (e.g., paraffins) have numerous limitations. For instance, separation technologies that utilize distillation require high energy and costly equipment. Furthermore, distillation is highly energy intensive when there are very small differences in boiling points between olefins and non-olefins.

As such, membrane-based systems have been considered as a substitute for distillation-based technologies for separating olefins from non-olefins. However, many membrane-based systems have poor olefin/non-olefin separation properties due to small size and solubility differences between olefins and non-olefins.

Supported ionic liquid membranes containing transition metal ions have been used to separate paraffins and olefins through facilitated transport. In such systems, both olefin permeability and olefin/paraffin selectivity are increased due to reversible interaction between the olefin and metal ions through $\pi$ bond complexation, which increases the olefin solubility but not the paraffin solubility.

However, the use of transition metal ions in the separation of olefins from paraffins through facilitated transport has numerous limitations. For instance, transition metal ions (e.g., silver ions in silver carriers) are subject to reduction by reducing agents, such as hydrogen gas. Such reduction affects a membrane's lifetime because the reduced versions of the transition metal ions become unavailable for facilitated transport of olefins. This in turn leads to a reduction in the olefin/paraffin selectivity and the consequent undesirability of such systems for commercial use.

In particular, silver ions used in facilitated transport membranes are known to be irreversibly reduced to elemental silver upon exposure to hydrogen gas. Therefore, membranes containing silver salts have been deemed undesirable for facilitated transport of olefins if the hydrogen instability issue cannot be resolved (Merkel et al., *J Memb. Sci.*, 447:177-189, 2013). Even when efforts are taken to remove all hydrogen gas before contacting the silver-containing membranes, some hydrogen gas remains and eventually reduces the efficacy of the membrane.

Present technologies to mitigate or address transition metal ion reduction by hydrogen gas are costly and time consuming. For instance, membranes containing reduced transition metal ions could be regenerated. However, such methods would require the membranes to be taken offline.

Likewise, small amounts of a hydrogen peroxide and nitric acid solution could be added to the facilitated solvent to stabilize the transition metal ions (e.g., silver ions) against reduction. However, the hydrogen peroxide and nitric acid are consumed and must be continuously replenished. This in turn results in additional costs.

As such, a need exists for improved methods and systems for separating olefins from a mixture in a selective and continuous manner where the substantial reduction of metal ions by reducing agents are prevented. Various embodiments of the present disclosure address this need.

In some embodiments, the present disclosure pertains to methods of separating olefins from a mixture that includes olefins and non-olefins. In some embodiments illustrated in FIG. 1A, the methods of the present disclosure can include one or more of the following steps: providing a mixture containing olefins and non-olefins (step 10); associating the mixture with a support embedded with ionic liquids and metal ions (step 12) such that the ionic liquids prevent the substantial reduction of the metal ion by reducing agents (step 14), and the metal ions mediate the transport of the olefin through the support by selectively and reversibly coupling with the olefin (step 16). In additional embodiments, the methods of the present disclosure also include a step of reusing the support in order to separate additional olefins from a mixture (step 18). In some embodiments, the reusing occurs by continuously associating a mixture with the support to produce a continuously flowing permeate stream.

Figure 1B:
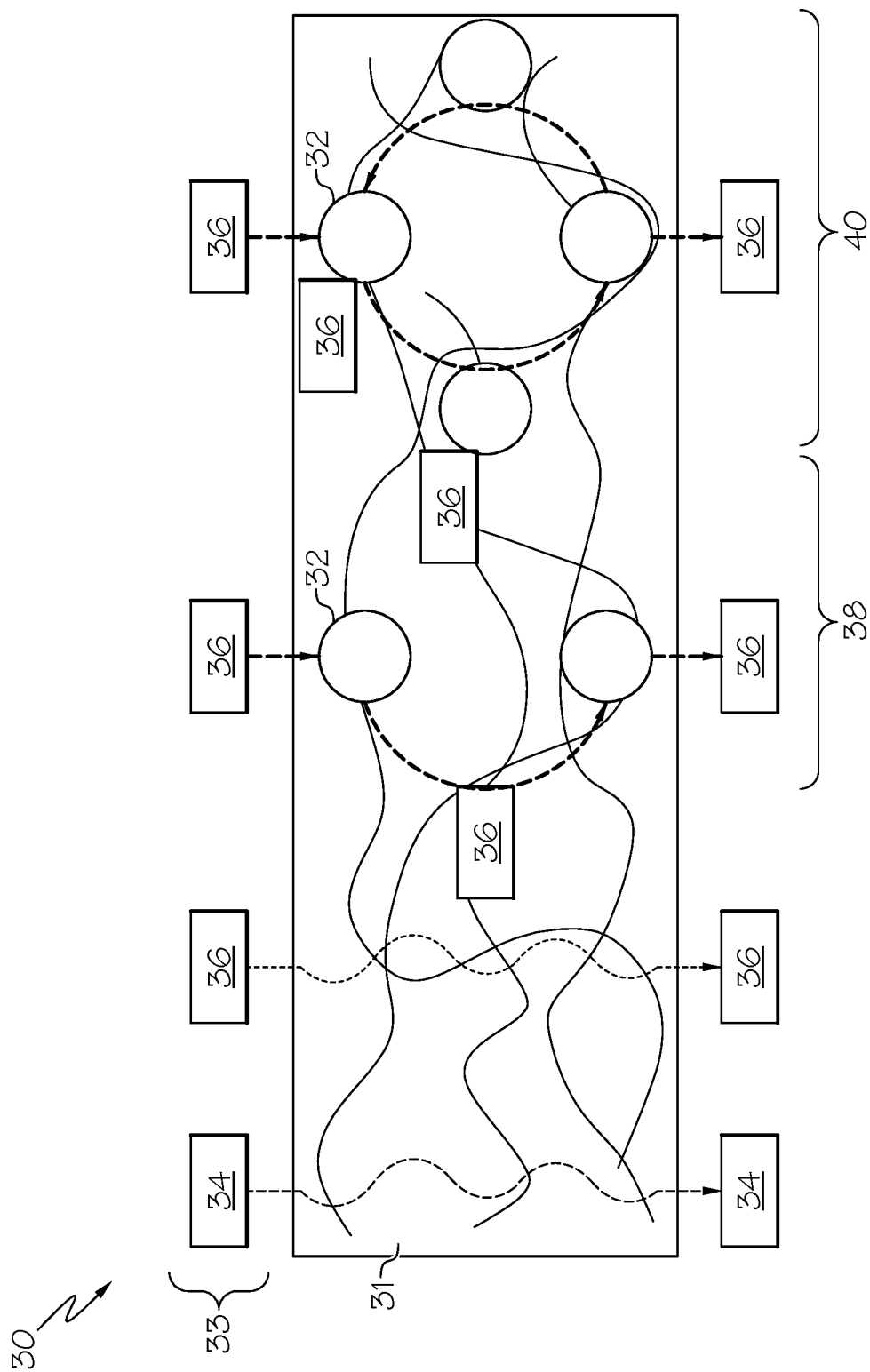
FIG. 1B illustrates a system for separating olefins from a mixture.

Additional embodiments of the present disclosure pertain to systems for separating olefins from a mixture that includes olefins and non-olefins. The systems of the present disclosure generally include a support embedded with an ionic liquid and a metal ion, where the ionic liquid prevents the substantial reduction of the metal ion by reducing agents. An example of a system of the present disclosure is illustrated as system 30 in FIG. 1B. System 30 generally includes support 31 embedded with metal ions 32 and ionic liquids such that the ionic liquids prevent the substantial reduction of the metal ions by reducing agents.

In operation, support 31 can become associated with mixture 33, which contains non-olefins 34 and olefins 36. Thereafter, metal ions 32 mediate the transport of olefins 36 through support 31 by selectively and reversibly coupling with olefins 36. During the process, ionic liquids prevent the substantial reduction of metal ions 32 by reducing agents, such as hydrogen gas in mixture 33. In some embodiments illustrated in region 38, transport can occur when metal ions 32 serve as fixed site carriers of olefins 36. In some embodiments illustrated in region 40, transport can occur when metal ions 32 serve as mobile carriers of olefins 36.

As set forth in more detail herein, the systems and methods of the present disclosure can have numerous embodiments. In particular, the systems and methods of the present disclosure can be utilized to separate various olefins from various non-olefins in various mixtures by utilizing various supports, metal ions, and ionic liquids. Furthermore, the ionic liquids of the present disclosure can prevent the substantial reduction of metal ions by various reducing agents in various manners. Moreover, the metal ions of the present disclosure can mediate the transport of olefins through supports through various mechanisms.

Mixtures

In the present disclosure, mixtures generally refer to mixtures that include olefins and non-olefins. The mixtures of the present disclosure may be in various forms. For instance, in some embodiments, the mixtures of the present disclosure may be in gaseous form. In some embodiments, the mixtures of the present disclosure may be in liquid form. In some embodiments, the mixtures of the present disclosure may be in gaseous and liquid forms.

The mixtures of the present disclosure can include various types of non-olefins. For instance, in some embodiments, the non-olefins in the mixture include, without limitation, hydrocarbons, paraffins (i.e., alkanes), and combinations thereof. In some embodiments, the non-olefins in the mixture include paraffins. In some embodiments, the non-olefins in the mixture include, without limitation, propane, ethane, butane, and combinations thereof.

The mixtures of the present disclosure can also include various types of olefins (i.e., alkenes). For instance, in some embodiments, the olefins in the mixture include dehydrogenated versions of the non-olefins. In some embodiments, the olefins in the mixture include dehydrogenated paraffins.

The mixtures of the present disclosure can also include various reducing agents. For instance, in some embodiments, the reducing agents include hydrogen gas. In some embodiments, the reducing agents include hydrogen sulfide. In some embodiments, the reducing agents include aldehydes.

The mixtures of the present disclosure can include various amounts of reducing agents. For instance, in some embodiments, the mixtures of the present disclosure include trace amounts of reducing agents. In some embodiments, the reducing agents constitute less than 5 wt % of the mixture, less than 1 wt % of the mixture, less than 0.1 wt % of the mixture, less than 0.01 wt % of the mixture, less than 0.001 wt % of the mixture, less than 0.0001 wt % of the mixture, or less than 0.00001 wt % of the mixture.

In some embodiments, the mixtures of the present disclosure may include minimal amounts of metal ion stabilizing agents, such as hydrogen peroxide or nitric acid. For instance, in some embodiments, metal ion stabilizing agents constitute less than 5 wt % of the mixture, less than 4 wt % of the mixture, less than 3 wt % of the mixture, less than 2 wt % of the mixture, less than 1 wt % of the mixture, less than 0.5 wt % of the mixture, less than 0.1 wt % of the mixture, less than 0.01 wt % of the mixture, or less than 0.001 wt % of the mixture. In some embodiments, the mixtures of the present disclosure lack any metal ion stabilizing agents.

The mixtures of the present disclosure can be derived from various sources. For instance, in some embodiments, the mixtures may be derived from shale gas resources.

In some embodiments, the mixtures are provided in untreated form. In some embodiments, the mixtures undergo a dehydrogenation step to result in the formation of olefins from the non-olefins in the mixture.

Dehydrogenation can occur in various manners. For instance, in some embodiments, the dehydrogenation can occur by catalytic dehydrogenation.

In some embodiments, the dehydrogenation step generates hydrogen gas. As such, in some embodiments, the methods of the present disclosure also include a step of removing at least some of the generated hydrogen gas from the mixture. In some embodiments, a majority of the generated hydrogen gas is removed from the mixture. In some embodiments, at least 50% of the generated hydrogen gas is removed from the mixture. In some embodiments, at least 75% of the generated hydrogen gas is removed from the mixture. In some embodiments, at least 90% of the generated hydrogen gas is removed from the mixture. In some embodiments, at least 95% of the generated hydrogen gas is removed from the mixture. In some embodiments, at least 99% of the generated hydrogen gas is removed from the mixture.

Supports

The methods and systems of the present disclosure can utilize various types of supports. In some embodiments, the supports of the present disclosure are capable of supporting ionic liquids and metal ions. For instance, in some embodiments, the support is a porous and solid support. In some embodiments, the support is in the form of porous membranes. In some embodiments, the supports include, without limitation, porous supports, ceramic-based supports, organic supports, polymer-based supports, metal-based supports, aluminum oxide-based supports, inorganic supports, composites, polymer composites, ionic liquid/polymer composites, membranes thereof, and combinations thereof. In some embodiments, the supports include anopore membrane discs.

In some embodiments, the supports of the present disclosure are in the form of supported ionic liquid porous membranes. In some embodiments, the ionic liquid is held within pores of the supported ionic liquid porous membranes by capillary forces.

In some embodiments, the supports of the present disclosure are in the form of a composite, such as a polymer composite or an ionic liquid/polymer composite. In some embodiments, the ionic liquid is dispersed throughout the composite.

In some embodiments, the supports of the present disclosure include inorganic supports. In some embodiments, the inorganic supports include, without limitation, α-alumina, glass, titania, zirconia, carbon, silicon carbide, clays, silicate minerals, aerogels, supported aerogels, supported silica, titania, zirconia, and combinations thereof.

In some embodiments, the supports of the present disclosure include ceramic-based supports. In some embodiments, the ceramic-based supports include aluminum oxide ($Al_2O_3$).

In some embodiments, the supports of the present disclosure include metal-based supports. In some embodiments, the metal-based supports include, without limitation, stainless steel, nickel-based alloys (e.g., Inconel or Hastalloy), Fecralloy, chromium, titanium, and combinations thereof.

The metal-based supports of the present disclosure may be in various forms. For instance, in some embodiments, the metal-based supports of the present disclosure may be in the form of a fibrous mesh (e.g., a woven or non-woven fibrous mesh), sintered metal particles, a combination of fibrous metal with sintered metal particles, and combinations of such forms. In some embodiments, the metal-based support includes sintered metal particles.

In some embodiments, the supports of the present disclosure include organic supports. In some embodiments, the organic supports include polymer-based supports. The polymer-based supports of the present disclosure may include various polymers. For instance, in some embodiments, the polymers include, without limitation, a cross-linked polymer, a phase separated polymer, a porous condensed polymer, blends thereof, and combinations thereof. In some embodiments, the polymers include, without limitation, polyamides, polyimides, polypyrrolones, polyesters, sulfone-based polymers, nitrile-based polymers, polymeric organosilicones, fluorinated polymers, polyolefins, copolymers thereof, blends thereof, and combinations thereof. In some embodiments, the polymers include, without limitation, polydimethylsiloxane, polydiethylsiloxane, polydi-isopropylsiloxane, polydiphenylsiloxane, polyethersulfone, polyphenylsulfone, polysulfone, polyacrylonitrile, polyvinylidene fluoride, polyamide, polyimide, polyetherimide, polyetheretherketone, polyphenylene oxide, polybenzimidazole, polypropylene, polyethylene, polyethylene oxide, partially fluorinated derivatives thereof, perfluorinated derivatives thereof, sulfonated derivatives thereof, copolymers thereof, blends thereof, and combinations thereof. In some embodiments, the polymers include polysulfone, polyethersulfone, and combinations thereof.

The supports of the present disclosure can include various surface areas. For instance, in some embodiments, the supports of the present disclosure include surface areas that range from about 0.01 $m^2$ to about 1,000 $m^2$. In some embodiments, the supports of the present disclosure include surface areas that range from about 0.02 $m^2$ to about 750 $m^2$.

In some embodiments, the supports of the present disclosure include surface areas that range from about 0.025 m$^2$ to about 500 m$^2$. In some embodiments, the supports of the present disclosure include surface areas that range about 1 m$^2$ to about 100 m$^2$. In some embodiments, the supports of the present disclosure include surface areas that are more than about 1,000 m$^2$.

The supports of the present disclosure can also include various thicknesses. For instance, in some embodiments, the supports of the present disclosure include thicknesses that range from about 0.1 to about 200 µm. In some embodiments, the supports of the present disclosure include thicknesses that range from about 2 µm to about 175 µm. In some embodiments, the supports of the present disclosure include thicknesses that range from about 10 µm to about 100 µm. In some embodiments, the supports of the present disclosure include thicknesses that range from about 50 µm to about 100 µm. In some embodiments, the supports of the present disclosure include thicknesses of about 60 µm.

The supports of the present disclosure can also include various porosities. For instance, in some embodiments, the supports of the present disclosure have pores with diameters greater than about 0.01 µm, greater than about 0.02 µm, greater than about 0.05 µm, greater than about 0.07 µm, greater than about 0.1 µm, greater than about 0.2 µm, greater than about 0.5 µm, greater than about 0.7 µm, greater than about 1.0 µm, greater than about 1.2 µm, greater than about 1.5 µm, greater than about 1.7 µm, greater than about 2.0 µm, greater than about 2.2 µm, greater than about 2.5 µm, greater than about 2.7 µm, or greater than about 3.0 µm. In some embodiments, the supports of the present disclosure have pores with diameters of less than about 3.0 µm.

In some embodiments, the supports of the present disclosure have pores with diameters ranging from about 1 nm to about 500 nm. In some embodiments, the supports of the present disclosure have pores with diameters ranging from about 1 nm to about 100 nm. In some embodiments, the supports of the present disclosure have pores with diameters ranging from about 1 nm to about 50 nm. In some embodiments, the supports of the present disclosure have pores with nominal pore size of about 20 nm in diameter.

The supports of the present disclosure can include various structures. For instance, in some embodiments, the supports of the present disclosure can be in the form of at least one of a flat disk, a tube, a spiral wound, or a hollow fiber base. The base can be formed from any suitable material. Examples of suitable materials include, without limitation, fibrous materials, a mesh (e.g., a metal or polymer mesh), a woven or non-woven fabric, a glass, a fiberglass, a resin, a screen (e.g., a metal or polymer screen), and combinations thereof.

Ionic Liquids

Ionic liquids generally refer to salts that have a melting point at or below 100° C. The systems and methods of the present disclosure can utilize various types of ionic liquids. For instance, in some embodiments, the ionic liquids include, without limitation, cations, anions, organic ionic liquids, organic anions, organic cations, inorganic ionic liquids, inorganic cations, inorganic anions, mixtures thereof, and combinations thereof. In some embodiments, the ionic liquids include a mixture of different types of ionic liquids.

In some embodiments, the ionic liquids of the present disclosure include at least one type of cation and at least one type of anion. In some embodiments, the ionic liquids of the present disclosure include at least one organic cation (i.e., an organic group containing cation). In some embodiments, the organic cation is formed by alkylation of a neutral organic species capable of holding a positive charge when a suitable anion is present. In some embodiments, the organic cation can be a complex polyatomic cation, which contains at least an organic group bonded to a heteroatom.

The ionic liquids of the present disclosure can include various types of organic cations. For instance, in some embodiments, the organic cations include, without limitation, ionic liquids that contain one or more heteroatoms (e.g., nitrogen, phosphorus, oxygen, or sulfur heteroatom(s)). In some embodiments, the organic cations can include a linear, branched, or cyclic compound with one or more heteroatoms.

In some embodiments, the organic cations can include quaternary ammonium compounds (QACs). In some embodiments, the organic cations can include quaternary phosphonium compounds. In some embodiments, the organic cations can include ternary sulfurous compounds.

In some embodiments, the organic cations can include heteroaryls. In some embodiments, the heteroaryls can include aliphatic heteroaryls. An aliphatic heteroaryl cation is a compound that includes at least one aliphatic moiety bonded to a heteroaryl moiety. In some embodiments, the aliphatic moiety can include, without limitation, alkyl groups, alkenyl groups, alkynyl groups, heteroalkyl groups, heteroalkenyl groups, heteroalkynyl groups, cycloalkyl groups, cycloalkenyl groups, heterocycloalkyl groups, heterocycloalkenyl groups, and combinations thereof.

In some embodiments, the heteroaryl moiety of a heteroaryl cation is an aryl group having a nitrogen atom and optionally one or more additional heteroatoms (e.g., nitrogen, oxygen, sulfur, phosphorous, or halonium). Examples of specific heteroaryl moieties that can be used in heteroaryl cations include, without limitation, substituted or unsubstituted benztriazoliums, substituted or unsubstituted benzimidazoliums, substituted or unsubstituted benzothiazoliums, substituted or unsubstituted pyridiniums, substituted or unsubstituted pyridaziniums, substituted or unsubstituted pyrimidiniums, substituted or unsubstituted pyraziniums, substituted or unsubstituted imidazoliums, substituted or unsubstituted pyrazoliums, substituted or unsubstituted oxazoliums, substituted or unsubstituted 1,2,3-triazoliums, substituted or unsubstituted 1,2,4-triazoliums, substituted or unsubstituted thiazoliums, substituted or unsubstituted piperidiniums, substituted or unsubstituted pyrrolidiniums, substituted or unsubstituted quinoliums, substituted or unsubstituted isoquinoliums, and combinations thereof.

In some embodiments, the heteroatom of the heteroaryl moiety of the heteroaryl cation is nitrogen, which can form a quaternary ammonium cation. When substituted, the substituents can be substituted with one or more groups including, without limitation, hydroxyl, halogen, acyl, alkyl, alkoxy, alkenyl, alkynyl, aryl, heteroaryl, aldehyde, amino, cyano, carboxylic acid, ester, ether, ketone, nitro, phosphonyl, silyl, sulfo-oxo, sulfonyl, sulfone, sulfoxide, thiol, and combinations thereof.

The following are further examples of heteroaryl cations that are suitable for use in the ionic liquids of the present disclosure:

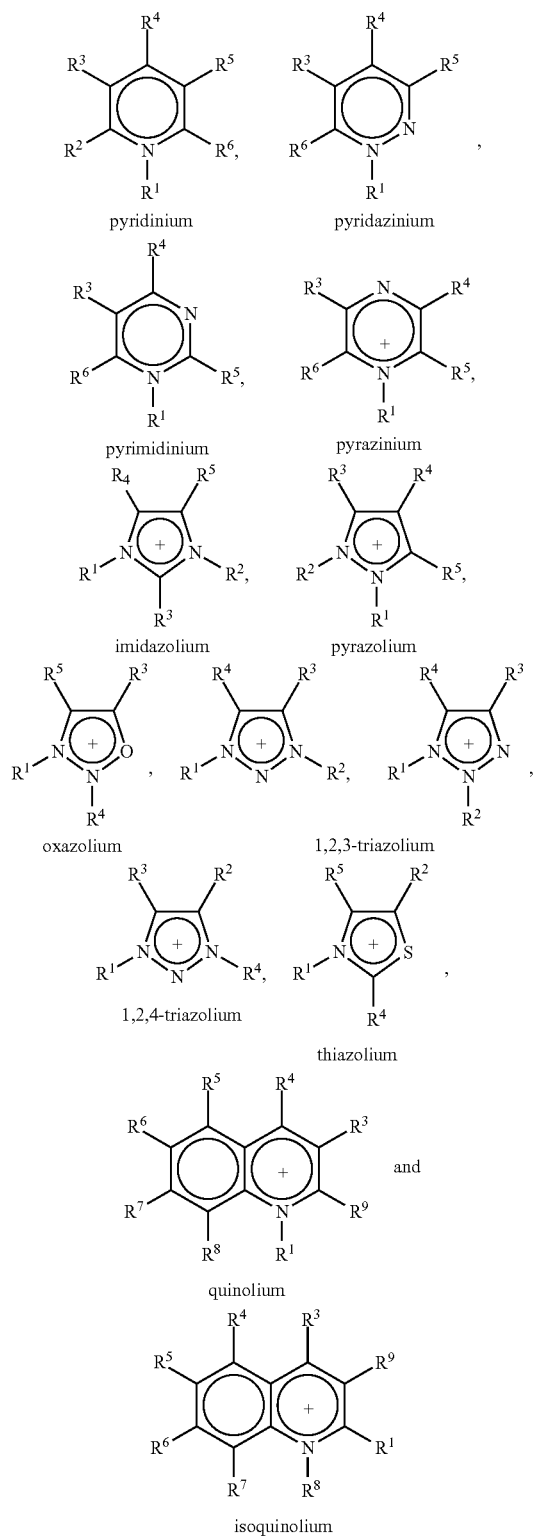

pyridinium, pyridazinium, pyrimidinium, pyrazinium, imidazolium, pyrazolium, oxazolium, 1,2,3-triazolium, 1,2,4-triazolium, thiazolium, quinolium, and isoquinolium In the aforementioned compounds, each $R^1$ and $R^2$ is, independently, a substituted or unsubstituted linear, branched, or cyclic $C_1$-$C_x$ alkyl, or substituted or unsubstituted linear, branched, or cyclic $C_1$-$C_x$ alkoxy; each $R^3$, $R^4$, $R^5$, $R^6$, $R^7$, $R^8$, and $R^9$ is, independently, hydrogen, substituted or unsubstituted linear, branched, or cyclic $C_1$-$C_x$ alkyl, substituted or unsubstituted linear, branched, or cyclic $C_1$-$C_x$ alkoxy, substituted or unsubstituted linear or branched, $C_1$-$C_x$ alkoxyalkyl, $NO_2$, $NH_2$, or CN. In some embodiments, at least one of $R^1$-$R^9$ is a $C_{4\text{-}10}$ alkyl.

In some embodiments, suitable organic cations include cyclic, nonaromatic compounds with one or more heteroatoms. Examples of such heterocyclic compounds are as follows:

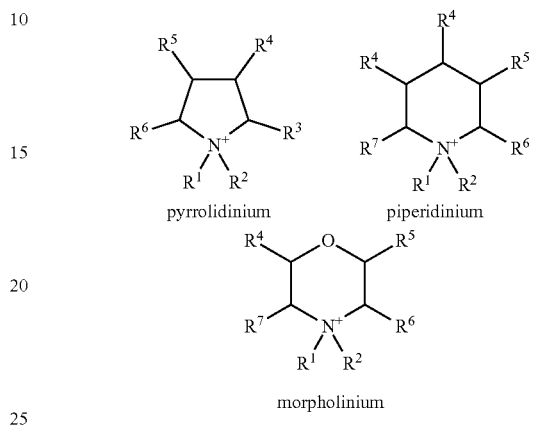

pyrrolidinium, piperidinium, morpholinium

In the aforementioned compounds, each $R^1$ and $R^2$ is, independently, a substituted or unsubstituted linear, branched, or cyclic $C_1$-$C_x$ alkyl, or substituted or unsubstituted linear, branched, or cyclic $C_1$-$C_x$ alkoxy; each $R^3$, $R^4$, $R^5$, $R^6$, $R^7$, $R^8$, and $R^9$ is, independently, hydrogen, substituted or unsubstituted linear, branched, or cyclic $C_1$-$C_x$ alkyl, substituted or unsubstituted linear, branched, or cyclic $C_1$-$C_x$ alkoxy, or substituted or unsubstituted linear or branched, $C_1$-$C_x$ alkoxyalkyl. In some embodiments, at least one of $R^1$-$R^9$ is a $C_{4\text{-}x}$ alkyl. In some embodiments, the ionic liquid compositions include an ammonium cation of the structure $NR^1R^2R^3R^4$ or phosphonium cation of the structure $NR^1R^2R^3R^4$, wherein $R^1$, $R^2$, $R^3$, and $R^4$ are independently H, halogen, substituted or unsubstituted $C_1$-$C_x$ alkyl, substituted or unsubstituted $C_1$-$C_x$ cycloalkyl, or wherein, as valence permits, two or more of $R^1$, $R^2$, $R^3$, and $R^4$, together with the atoms to which they are attached, form a 3-10 membered cyclic moiety.

In some embodiments, x can be any number larger than 1, such as 2, 10, 12, 14, 16 or higher. In some embodiments, $R^1$, $R^2$, $R^3$, and $R^4$ are independently H or substituted or unsubstituted $C_1$-$C_x$ alkyl. In some embodiments, $R^1$, $R^2$, $R^3$, and $R^4$ are independently H or unsubstituted $C_4$-$C_x$ alkyl. In some embodiments, the organic cation can include $C_n$ alkylmethylimidazolium [$C_n$mim] where n is an integer of 1 or higher, such as integers from 1 to 8. For instance, in some embodiments, $C_{1\text{-}6}$ alkyl-methylimidazolium [$C_{1\text{-}6}$mim] can be used.

In some embodiments, the organic cation can include $C_n$ alkyldimethylimidazolium [$C_n$mmim] where n is an integer of 1 or higher, such as integers from 1 to 8. For instance, in some embodiments, the organic cation is $C_{1\text{-}6}$ alkyl-dimethylimidazolium [$C_{1\text{-}6}$mmim]. In more specific embodiments, the ionic liquid is 1-hexyl-2,3-dimethylimidazolium.

In some embodiments, the ionic liquids of the present disclosure include anions. The ionic liquids of the present disclosure can include numerous anions. For instance, in some embodiments, the anions include, without limitation, substituted or unsubstituted carbonates. In some embodiments, the carbonates include, without limitation, $R^{10}CO_2^-$, formate $HCO_2^-$, acetate $CH_3CO_2^-$ (also noted herein as

[OAc]), proprionate, $CH_3CH_2CO_2^-$, butyrate $CH_3CH_2CH_2CO_2^-$, benzylates, $C_6H_5CO_2^-$, and combinations thereof.

In some embodiments, the anions include substituted or unsubstituted sulfates. In some embodiments, the sulfates include, without limitation, $(R^{10}O)S(=O)_2O^-$, substituted or unsubstituted sulfonates, $R^{10}SO_3^-$, $(CF_3)SO_3$, and combinations thereof.

In some embodiments, the anions include substituted or unsubstituted phosphates. In some embodiments, the phosphates include $(R^{10}O)_2P(=O)O^-$. In some embodiments, the anions include substituted or unsubstituted carboxylates. In some embodiments, the carboxylates include $(R^{10}O)C(=O)O^-$. Non-limiting examples of $R^{10}$ include, without limitation, hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; seleno; and combinations thereof. In some embodiments, the anion is $C_{1-6}$ carboxylate.

In some embodiments, the anions that can be used in the ionic liquids of the present disclosure include, without limitation, halides (e.g., $F^-$, $Cl^-$, $Br^-$, and $F^-$), $CO_3^{2-}$, $HCO_3^-$, $NO_2^-$, $NO_3^-$, $SO_4^{2-}$, $CN^-$, $SCN^-$, $OCN^-$, arsenate (V), $AsX_6^-$, $AsF_6^-$, stibate(V) (antimony), $SbX_6^-$, $SbF_6^-$, $PF_6^-$, $^-P(CF_3CF_2)_3F_3$, $BF_4^-$, $B(CN)_4^-$, $^-BF_3(CF_2CF_3)$, and combinations thereof. In some embodiments, the anions include triflate (TfO; $CF_3SO_2^-$), $CF_3SO_3^-$, nonaflate (NfO; $CF_3(CF_2)_3SO_2^-$), bis(triflyl)amide (Tf_2N; $(CF_3SO_2)_2N^-$), $(CF_3)_2N^-$, trifluoroacetate (TFA; $CF_3CO_2^-$), biscyanoamide $(N(CN)_2)$, heptaflurorobutanoate (HB; $CF_3(CF_2)_3SO_2^-$), and combinations thereof. In some embodiments, the anions include, without limitation, substituted and unsubstituted imidazolates, 1,2,3-triazolates, 1,2,4-triazolates, benzimidazolates, and benz-1,2,3-triazolates, as shown herein:

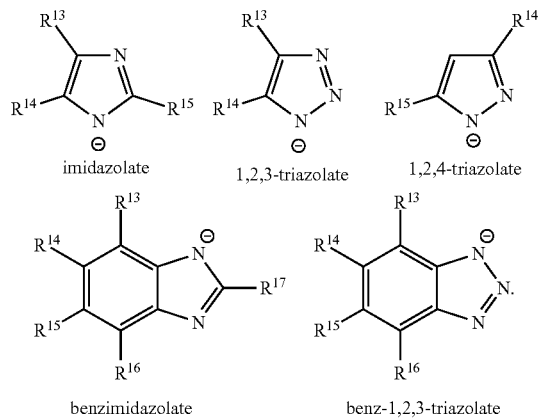

imidazolate    1,2,3-triazolate    1,2,4-triazolate benzimidazolate    benz-1,2,3-triazolate In some embodiments, $R^{13}$, $R^{14}$, $R^{15}$, $R^{16}$, $R^{17}$, and $(R^{13-17})$, when present, are independently H, a $C_1$-$C_x$, alkyl, a $C_1$-$C_x$, alkoxyalkyl group, a $C_1$-$C_x$ alkoxy group, or substituents such as nitro, amino, cyano, azido, alkyl nitro, alkyl amino, alkyl cyano, alkyl azido, alkoxy nitro, alkoxy amino, alkoxy cyano, and alkoxy azido.

In some embodiments, exemplary $C_1$-$C_8$ alkyl groups and $C_1$-$C_4$ alkyl groups include, without limitation, methyl, ethyl, propyl, iso-propyl, butyl, sec-butyl, iso-butyl, pentyl, iso-pentyl, hexyl, 2-ethylbutyl, 2-methylpentyl, and the like. In some embodiments, corresponding $C_1$-$C_6$ alkoxy groups contain the aforementioned $C_1$-$C_8$ alkyl group bonded to an oxygen atom that is also bonded to the cation ring. In some embodiments, an alkoxyalkyl group contains an ether group bonded to an alkyl group, and contains a total of up to six carbon atoms. In some embodiments, all R groups that are not required for anion formation can be H.

In more specific embodiments, suitable anions can include the following structures:

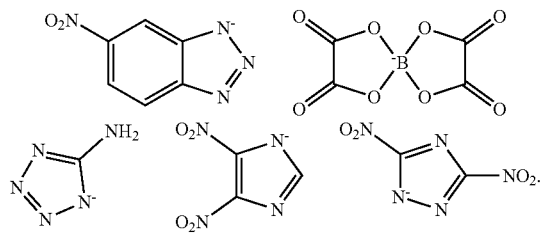

In some embodiments, the ionic liquid is a salt of an organic cation and an anion. In some embodiments, the ionic liquids include imidazolium-based ionic liquids. In some embodiments, the imidazolium-based ionic liquids include 1-hexyl-2,3-dimethylimidazolium bis(trifluoromethylsulfonyl)imide ionic liquid ([hmmim][Tf_2N]). In some embodiments, the imidazolium-based ionic liquids include a mixture of 1-Ethyl-3-methylimidazolium bis(trifluoromethylsulfonyl)imide ([emim][Tf_2N]) and 1-hexyl-3-methylimidazolium bis(trifluoromethylsulfonyl)imide ([hmim][Tf_2N]). In some embodiments, the imidazolium-based ionic liquids include, without limitation, 1-Ethyl-3-methylimidazolium bis(trifluoromethylsulfonyl)imide ([emim][Tf_2N]), 1-hexyl-3-methylimidazolium bis(trifluoromethylsulfonyl)imide ([hmim][Tf_2N]), 1-hexyl-2,3-dimethylimidazolium bis(trifluoromethylsulfonyl)imide ionic liquid ([hmmim][Tf_2N]), 1-hexyl-3-methylimidazolium trifluoromethanesulfonate ([hmim][TfO]), and combinations thereof. The use of additional ionic liquids can also be envisioned.

The ionic liquids of the present disclosure can include various viscosities. For instance, in some embodiments, the ionic liquids of the present disclosure have a viscosity such that they can permeate a support easily and yet stay in the support, even under pressure. In some embodiments, the ionic liquids of the present disclosure can have a viscosity at or below about 100 cP at 35° C., at or below about 90 cP at 35° C., at or below about 80 cP at 35° C., at or below about 70 cP at 35° C., at or below about 60 cP at 35° C., at or below about 50 cP at 35° C., at or below about 40 cP at 35° C., or at or below about 30 cP at 35° C.

In some embodiments, the ionic liquids of the present disclosure can have a viscosity of at or above about 20 cP at 35° C., at or above about 30 cP at 35° C., at or above about 40 cP at 35° C., at or above about 50 cP at 35° C., at or above about 60 cP at 35° C., at or above about 70 cP at 35° C., at or above about 80 cP at 35° C., at or above about 90 cP at 35° C., or at or above about 100 cP at 35° C. In more specific embodiments, the ionic liquids of the present disclosure can have a viscosity of from about 20 cP to about 100 cP at 35° C., from about 40 cP to about 80 cP at 35° C., from about 50 cP to about 90 cP at 35° C., or from about 30 cP to about 90 cP at 35° C.

In some embodiments, the ionic liquids of the present disclosure can have a viscosity of more than about 100 cP at 35° C. For instance, in some embodiments, the ionic liquids of the present disclosure can have a viscosity of at or above about 150 cP at 35° C., at or above about 200 cP at 35° C., at or above about 500 cP at 35° C., at or above about 600 cP at 35° C., at or above about 700 cP at 35° C., at or above about 800 cP at 35° C., at or above about 900 cP at 35° C., or at or above about 1,000 cP at 35° C.

The ionic liquids of the present disclosure can be embedded with supports in various manners. For instance, in some embodiments, the ionic liquids are within the pores of the supports and held in pores of the supports by capillary forces (e.g., embodiments where the support is in the form of supported ionic liquid porous membranes). In some embodiments, the ionic liquid is dispersed throughout the support (e.g., embodiments where the support is in the form of a composite, such as a polymer composite or an ionic liquid/polymer composite).

The ionic liquids of the present disclosure can serve various functions. For instance, in some embodiments, the ionic liquids of the present disclosure prevent the substantial reduction of the metal ion by reducing agents, such as hydrogen gas (e.g., hydrogen gas in a mixture) when they are used in accordance with the methods of the present disclosure to separate olefins from a mixture. In some embodiments, the ionic liquids of the present disclosure prevent the reduction of at least 85% of the metal ions associated with the support after at least about 24 hours of continuous use in accordance with the methods of the present disclosure. In some embodiments, the ionic liquids of the present disclosure prevent the reduction of at least 90% of the metal ions associated with the support after least about 24 hours of continuous use in accordance with the methods of the present disclosure. In some embodiments, the ionic liquids of the present disclosure prevent the reduction of at least 95% of the metal ions associated with the support after at least about 24 hours of continuous use in accordance with the methods of the present disclosure. In some embodiments, the ionic liquids of the present disclosure prevent the reduction of at least 99% of the metal ions associated with the support after at least about 24 hours of continuous use in accordance with the methods of the present disclosure.

Metal Ions

The systems and methods of the present disclosure can utilize various types of metal ions. For instance, in some embodiments, the metal ions include, without limitation, transition metal ions, silver ions, copper ions, nickel ions, iron ions, manganese ions, zinc ions, and combinations thereof. In some embodiments, the metal ions of the present disclosure include silver ions, such as $Ag^+$. In some embodiments, the metal ions of the present disclosure include copper ions, such as $Cu^+$.

In more specific embodiments, the metal ions of the present disclosure include silver ions. In some embodiments, the metal ions of the present disclosure are in the form of silver salts, which can dissociate in ionic liquids to form silver ions. In some embodiments, the silver salt can be a salt of silver and anyone of the anions disclosed herein. In some embodiments, the anion corresponds to the anion of the ionic liquid. For example, in some embodiments where the ionic liquid is 1-hexyl-2,3-dimethylimidazolium bis(trifluoromethylsulfonyl)imide, and thus bis(trifluoromethylsulfonyl) imide is the anion of the ionic liquid, then silver bis(trifluoromethylsulfonyl)imide can be used.

In some embodiments, the silver salts of the present disclosure can include, without limitation, $AgF$, $AgCl$, $AgBr$, $AgI$, $Ag_2CO_3$, $AgHCO_3$, $AgNO_2$, $AgNO_3$, $Ag_2SO_4$, $AgCN$, $AgSCN$, $AgOCN$, $AgAsX_6$, $AgAsF_6$, $AgSbX_6$, $AgSbF_6$, $AgPF_6$, $AgP(CF_3CF_2)_3F_3$, $AgBF_4$, $AgB(CN)_4$, $AgBF_3$ $(CF_2CF_3)$, $AgTfO$, $AgCF_3SO_3$, $AgNfO$, $AgTf_2N$, $Ag(CF_3)_2N$, $AgCF_3CO_2$, $AgN(CN)_2$, $AgCF_3(CF_2)_3SO_2$, and combinations thereof.

The systems of the present disclosure can include various amounts of metal ions. For instance, in some embodiments, the metal ions are in an amount of from about 0.1 wt % to about 50 wt % of a mixture. In some embodiments, the metal ions are in an amount of from about 0.1 wt % to about 25 wt % of a mixture. In some embodiments, the metal ions are in an amount of from about 0.1 wt % to about 10 wt % of a mixture. In some embodiments, the metal ions are in an amount of 1, 5, 10, 15, 20, 25, or 30 wt % of a mixture.

The metal ions of the present disclosure can be embedded with supports in various manners. For instance, in some embodiments, the metal ions of the present disclosure are dissolved in ionic liquids. In some embodiments, the metal ions of the present disclosure are dispersed throughout a support. In some embodiments, the metal ions of the present disclosure are dispersed throughout a support in the form of individual atoms. In some embodiments, the metal ions of the present disclosure are not in the form of any particles, such as nanoparticles. In some embodiments, the metal ions of the present disclosure are fixed at a location within the support (e.g., embodiments where the support is a composite, such as an ionic liquid/polymer composite). In some embodiments, the metal ions of the present disclosure are mobile within the support (e.g., embodiments where the support is a supported ionic liquid porous membrane).

Association of Mixtures to be Separated with Supports

Various methods may be utilized to associate mixtures with a support. For instance, in some embodiments, the associating occurs by contacting the mixture with the support.

The association of mixtures with a support can occur under various conditions. For instance, in some embodiments, the association can occur in the presence of reducing agents, such as hydrogen gas. In some embodiments, the association occurs in the presence of trace amounts of reducing agents, such as reducing agents that constitute less than 5 wt %, less than 1 wt %, less than 0.1 wt %, less than 0.01 wt %, less than 0.001 wt %, less than 0.0001 wt %, or less than 0.00001 wt % of the mixture.

In some embodiments, the methods of the present disclosure can also include a step of removing various amounts of reducing agents (e.g., hydrogen gas) from a mixture prior to associating the mixture with a support. However, in some embodiments, reducing agents are not removed from the mixture prior to associating the mixture with a support.

In some embodiments, the association occurs in the absence of substantial amounts of metal ion stabilizing agents, such as hydrogen peroxide or nitric acid. For instance, in some embodiments, the association occurs under conditions where metal ion stabilizing agents constitute less than 5 wt %, less than 4 wt %, less than 3 wt %, less than 2 wt %, less than 1 wt %, less than 0.5 wt %, less than 0.1 wt %, less than 0.01 wt %, or less than 0.001 wt % of the mixture.

The association of mixtures with a support can occur under various temperatures. For instance, in some embodiments, the association can occur at room temperature. In some embodiments, the association can occur above room temperature. In some embodiments, the association can occur at more than about 20° C., more than about 30° C., more than about 40° C., more than about 50° C., more than about 60° C., more than about 70° C., more than about 80°

C., more than about 90° C., more than about 100° C., more than about 110° C., more than about 120° C., or more than about 200° C.

In some embodiments, the methods of the present disclosure also include a step of heating the mixture prior to their association with a support. For instance, in some embodiments, the mixtures may be heated in order to reach one or more of the aforementioned temperatures.

Transport of Olefins Through the Support by Metal Ions

The metal ions of the present disclosure can mediate the transport of olefins through a support by selectively and reversibly coupling with the olefin. Without being bound by theory, the aforementioned transport can occur through various mechanisms.

For instance, in some embodiments, the olefins are separated from the non-olefins by differential transport through the support. In some embodiments, the coupling of metal ions with olefins occurs by a reversible interaction between the olefin and the metal ion through π bond complexation. In some embodiments, the metal ions serve as fixed site carriers of the olefins through the support (e.g., fixed site carriers shown in region 38 of FIG. 1B). In some embodiments, the metal ions serve as mobile carriers of the olefins through the support (e.g., mobile carriers shown in region 40 of FIG. 1B).

The coupling of metal ions with olefins can have various effects on the transport of olefins through a support. For instance, in some embodiments, the coupling increases the solubility of the olefins with respect to the non-olefins, thereby improving the transport of the olefins through the support.

Moreover, the ionic liquids of the present disclosure improve the transport of olefins through a support by preventing the substantial reduction of metal ions by reducing agents, such as hydrogen gas. In some embodiments, this results in the stabilization of metal ions by ionic liquids and a maintenance of olefin/non-olefin selectivity. For instance, in some embodiments, metal ions can remain stable for up to four days under harsh hydrogen permeation tests (e.g., 28 psi $H_2$, 35° C.) with only an approximate 12% reduction in propylene/propane selectivity after four days of hydrogen permeation tests.

Applications and Advantages

The present disclosure provides simplified systems and methods for separating olefins from non-olefins in a more effective manner. For instance, in some embodiments, a decrease in the reduction of metal ions in a support can increase a support's lifetime and enable higher olefin permeability and olefin/non-olefin selectivity.

In some embodiments, the systems and methods of the present disclosure provide an olefin/non-olefin selectivity of at least about 3 at 35° C., at least about 4 at 35° C., at least about 5 at 35° C., at least about 6 at 35° C., at least about 7 at 35° C., at least about 8 at 35° C., at least about 9 at 35° C., or at least about 10 at 35° C. In some embodiments, the systems and methods of the present disclosure can have a change in olefin/non-olefin selectivity of less than about 10% over 2 days, less than about 9% over 2 days, less than about 8% over 2 days, less than about 7% over 2 days, less than about 6% over 2 days, less than about 5% over 2 days, less than about 4% over 2 days, less than about 3% over 2 days, less than about 2% over 2 days, or less than about 1% over 2 days.

Furthermore, since the ionic liquids of the present disclosure provide a stable environment for the metal ions, the systems and methods of the present disclosure do not require the use of other materials or processing steps to increase support lifetime with respect to metal ion reduction by reducing agents. Moreover, the ionic liquids and metal ions of the present disclosure can be easily prepared and utilized with various supports.

As such, the systems and methods of the present disclosure can have numerous applications. For instance, in some embodiments, the systems and methods of the present disclosure can be utilized for the long-term and continuous separation of olefins from numerous olefin-containing mixtures without significant reduction of olefin/non-olefin selectivity, and without taking the membrane off-line for replenishment or regeneration of transition metal ions.

Moreover, the methods and systems of the present disclosure can be utilized to separate olefins from non-olefins in various mixtures, such as gas feedstocks that have a low concentration of hydrogen. In some embodiments, the methods and systems of the present disclosure can be utilized for use in the transformation of light hydrocarbons from shale gas resources into liquid fuels. In more specific embodiments, the methods and systems of the present disclosure can be utilized to separate olefins from paraffins after the catalytic dehydrogenation of paraffin into olefin during an industrial process that produces a mixture of olefin, unconverted paraffin, and hydrogen gas.

In additional embodiments, the systems and methods of the present disclosure can be used to remove olefins from paraffins as part of a two-step separation following the catalytic dehydrogenation of paraffins. The first step would involve removing the hydrogen gas produced from the catalytic dehydrogenation of paraffins, and the second step would involve removing the olefin from unconverted paraffin using a system of the present disclosure (e.g., a facilitated transport membrane made from silver ions dissolved in ionic liquid and embedded with a porous support). In some embodiments, such a stream may be contaminated by any unremoved hydrogen from step one.

ADDITIONAL EMBODIMENTS

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Silver Carriers Stabilized by Ionic Liquids Under Presence of Hydrogen Gas In this Example, Applicants demonstrate that silver ions dissolved in ionic liquids and embedded with porous supports are stable upon hydrogen exposure. In particular, Applicants demonstrate in this Example that silver ions dissolved in 1-hexyl-2,3-dimethylimidazolium bis(trifluoromethylsulfonyl)imide ionic liquid ([hmmim][Tf$_2$N]) and embedded in a microporous aluminum oxide membrane are stable up to four days under harsh hydrogen permeation tests (28 psi $H_2$, 35° C.) with only an approximate 12% reduction in propylene/propane selectivity after four days of hydrogen permeation tests.

52 mg of silver bis(trifluoromethylsulfonyl)imide (purchased from Alfa Aesar) was dissolved in 200 mg of 1-hexyl-2,3-dimethylimidazolium bis(trifluoromethylsulfonyl)imide synthesized in Applicants' laboratory (experimental details found in: Brennecke et al., High-Pressure Phase Behavior of Carbon Dioxide with Imidazolium-Based Ionic Liquids, J. *Phys. Chem. B* 20355-20365, 2004) under dark conditions using magnetic stirring until a homogenous solution was obtained.

Drops of the resulting solution were spread on a membrane surface using a syringe to completely cover the membrane. The membrane was a Whatman Anopore membrane disc (P/N 6809-5502) with a nominal pore size of 20 nm and a thickness of 60 µm. Complete wetting of the support was confirmed by observing a color change from white to transparent. A Kimwipe was used to gently wipe excess ionic liquid from the surface.

Propylene and propane pure gas permeability was measured at 35° C. and 0.145 bar transmembrane pressure using constant volume-variable pressure method described elsewhere (Lin et al., Permeation and diffusion, in: H. Czichos, L. Smith, T. Saito (Eds.), Springer-handb. Mater. Meas. Methods, Springer, 2006, pp. 371-387). The ideal selectivity was calculated as the ratio of propylene permeability to propane permeability. The membrane's performance was monitored for 3 days and the results are shown in Table 1 where $$1 \text{ Barrer} = 10^{-10} \frac{cm_{STP}^3 \cdot cm}{cm^2 \cdot s \cdot cm \text{ Hg}}.$$

TABLE 1

| Day | $C_3H_6$ Permeability (Barrer) | $C_3H_8$ Permeability (Barrer) | Selectivity |
| --- | --- | --- | --- |
| 1 | 283 | 40 | 7.1 |
| 2 | 285 | 42 | 6.8 |
| 3 | 284 | 41 | 6.9 |

As can be seen in Table 1, the membrane performance was stable over the 3 days that it was tested prior to hydrogen gas exposure. The membrane was then continuously exposed to hydrogen gas at a transmembrane pressure of 2.0 bar and 35° C. except for brief interruptions to measure the propylene and propane permeability at 0.145 bar transmembrane pressure to determine the propylene/propane selectivity after exposure to hydrogen. The results for 1 hour, 1 day and 4 days hydrogen exposure are shown in Table 2.

TABLE 2

| $H_2$ Permeation Time (Days) | $C_3H_6$ Permeability (Barrer) | $C_3H_8$ Permeability (Barrer) | Selectivity |
| --- | --- | --- | --- |
| 0.042 | 264 | 39 | 6.8 |
| 1 | 255 | 39 | 6.5 |
| 4 | 255 | 41 | 6.2 |

As can be seen in Table 2, the propylene/propane selectivity only drops approximately 10% after 4 days of hydrogen exposure. In a comparative example from the literature, a membrane made from a polymer doped with silver salt saw approximately a 65% drop in ethylene/ethane selectivity after 4 days of hydrogen exposure (Merkel, et al., Silver salt facilitated transport membranes for olefin/paraffin separations: Carrier instability and a novel regeneration method, *J. Memb. Sci.* 447:177-189, 2013).

Figure 2:
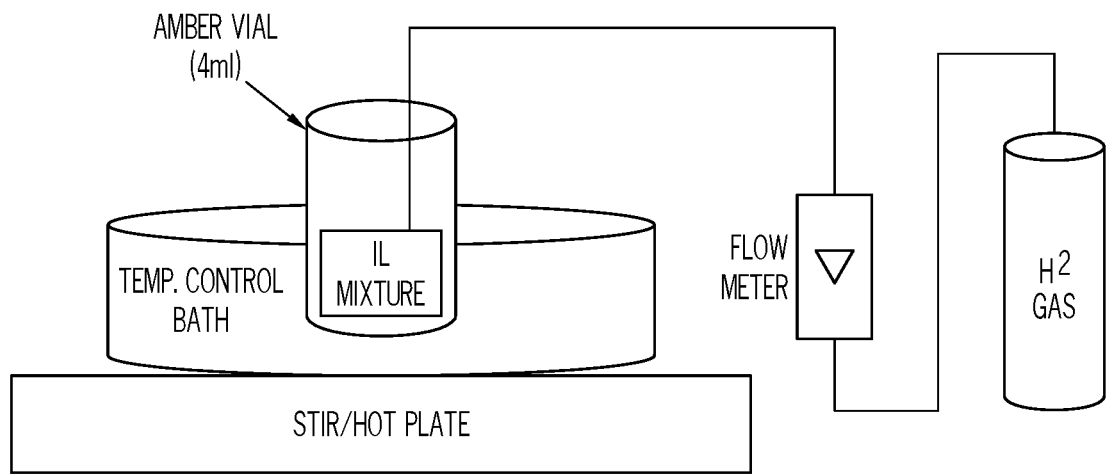
FIG. 2 provides an illustration of an experimental set-up for the hydrogen bubbling experiment described in Example 2.

Example 2. Silver Ion Stability in Ionic Liquids Under Hydrogen Gas Exposure To evaluate silver ion stability in ionic liquids under hydrogen gas exposure, silver ion reduction behavior under hydrogen gas bubbling was monitored in accordance with an experimental set up illustrated in FIG. 2. Two kinds of mixtures with two different anions were prepared: (1) a mixture of [Ag][Tf$_2$N] in [hmim][Tf$_2$N]; and (2) a mixture of [Ag][TfO] in [hmim][TfO] at concentrations of 0.5 M Ag$^+$. An amber vial of each mixture was prepared and placed in a temperature-controlled bath to maintain the temperature at 35° C. The flow of ultrapure hydrogen gas was introduced into the mixture for up to 1 hour and some portion of the sample was taken at each 20 minute interval to track the mixture reduction status.

Figure 3A:
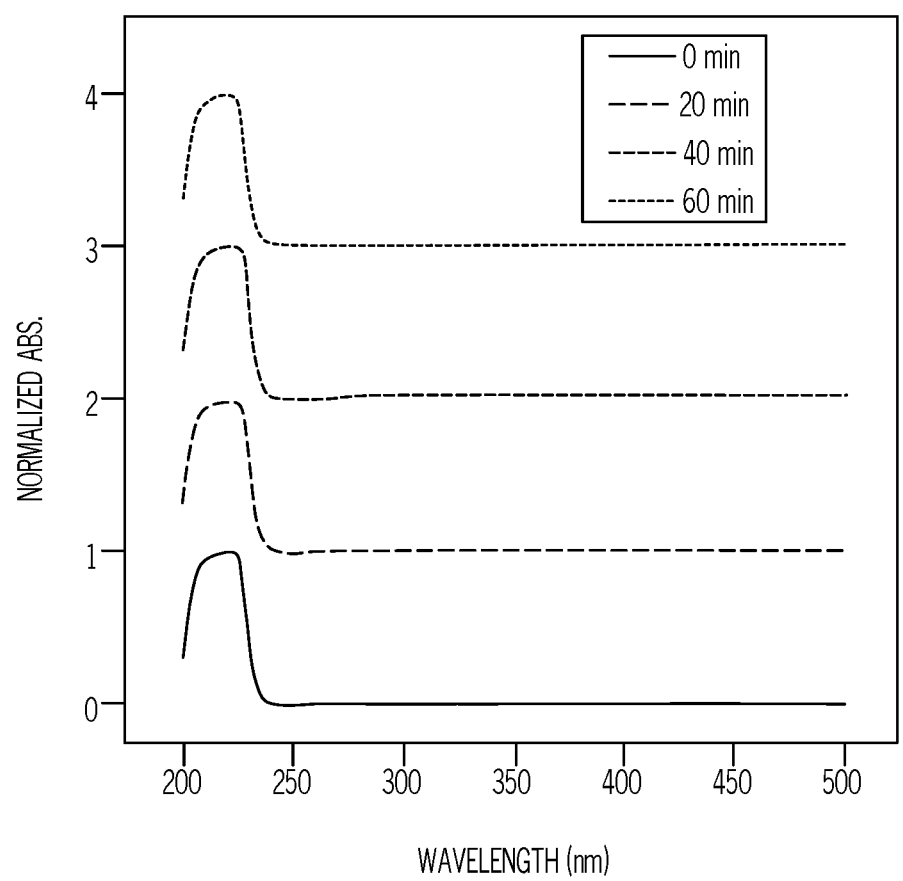
FIG. 3 shows a UV-vis spectroscopy on hydrogen bubbled samples from the experiment described in Example 2, including AgTfO in [hmim][TfO] (FIG. 3A) and AgTf$_2$N in [hmim][Tf$_2$N] (FIG. 3B).
Figure 3B:
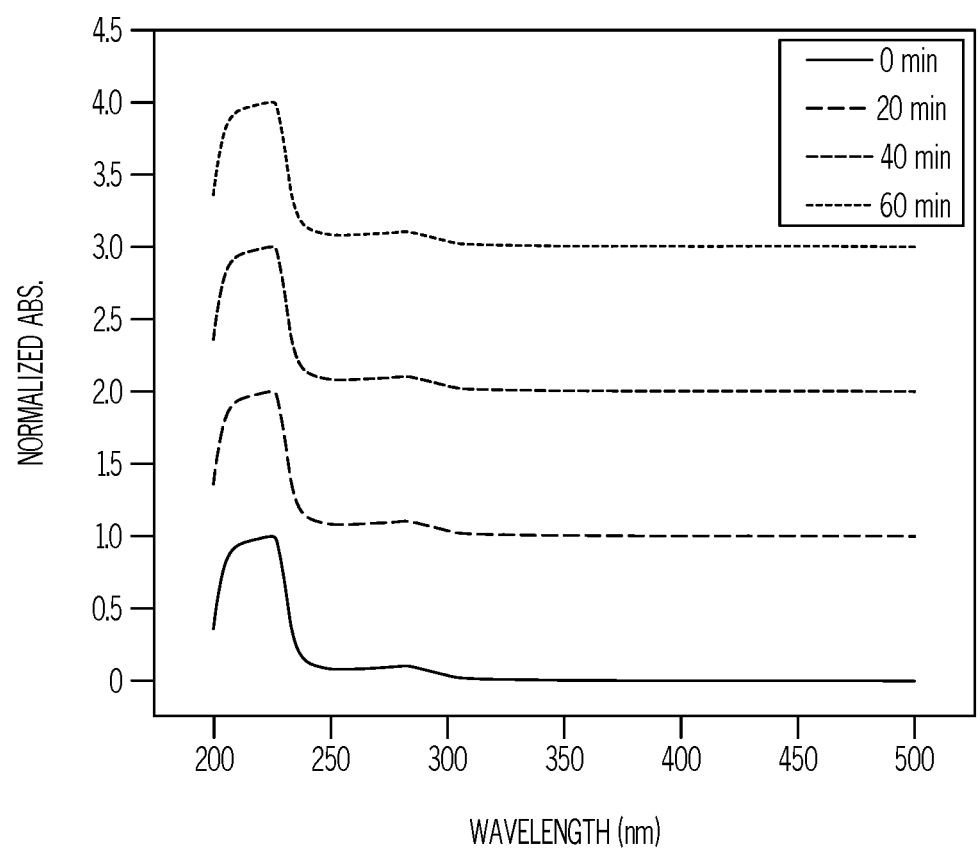

To examine the reduced silver presence, the UV-vis spectroscopy on the sampled mixture was conducted. The presence of the silver was checked by the intensity of the plasmon absorption peak (300–400 nm) of the silver metal. The results are shown in FIGS. 3A-B.

The plasmon absorption peak of silver metal did not appear in the TfO and Tf$_2$N mixtures for 60 minute hydrogen bubbled samples, indicating there are no silver particles formed by the exposure of hydrogen gas. The results showed the silver ion stability under hydrogen exposure with the presence of ionic liquid.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of separating olefins from a mixture comprising olefins and non-olefins, said method comprising:
   associating the mixture with a porous support, wherein the porous support is embedded with an ionic liquid and a transition metal ion, wherein the transition metal ion is dissolved in the ionic liquid in an amount of from about 0.1 wt. % to about 50 wt. %, wherein the ionic liquid prevents the substantial reduction of the transition metal ion by reducing agents, and wherein the transition metal ion mediates the transport of the olefin through the support by selectively and reversibly coupling with the olefin.

2. The method of claim 1, further comprising:
   a step of dehydrogenating the mixture prior to associating the mixture with the porous support, wherein the dehydrogenating forms olefins from the non-olefins and generates hydrogen gas; and
   a step of removing at least some of the generated hydrogen gas prior to associating the mixture with the support.

3. The method of claim 1, wherein the mixture comprises a gaseous mixture.

4. The method of claim 1, wherein the mixture comprises less than 0.5 wt % of metal ion stabilizing agents, and wherein the metal ion stabilizing agents are selected from the group consisting of hydrogen peroxide, nitric acid, and combinations thereof; and wherein the reducing agents comprise hydrogen gas, and wherein the reducing agents constitute less than 1 wt % of the mixture.

5. The method of claim 1, wherein the non-olefins comprise paraffins, and wherein the olefins comprise dehydrogenated versions of the non-olefins.

6. The method of claim 1, wherein the associating comprises contacting the mixture with the porous support, and wherein the coupling comprises a reversible interaction between the olefin and the transition metal ion through π bond complexation.

7. The method of claim 1, wherein the transition metal ions serve as fixed site or mobile carriers of the olefins through the porous support.

8. The method of claim 1, wherein the porous support is selected from the group consisting of ceramic-based supports, polymer-based supports, or metal-based supports, and combinations thereof; and wherein the transition metal ion is selected from the group consisting of silver ions, copper ions, nickel ions, iron ions, manganese ions, zinc ions, and combinations thereof.

9. The method of claim 1, wherein the porous support is in the form of a membrane, and wherein the ionic liquid is held within pores of the porous support by capillary forces.

10. The method of claim 1, wherein the porous support is in the form of a polymer composite, and wherein the ionic liquid is dispersed throughout the polymer composite.

11. The method of claim 1, wherein the ionic liquid comprises imidazolium-based ionic liquids, and wherein the imidazolium-based ionic liquids are selected from the group consisting of 1-Ethyl-3-methylimidazolium bis(trifluoromethylsulfonyl)imide ([emim][Tf$_2$N]), 1-hexyl-3-methylimidazolium bis(trifluoromethylsulfonyl)imide ([hmim][Tf$_2$N]), 1-hexyl-2,3-dimethylimidazolium bis(trifluoromethylsulfonyl)imide ionic liquid ([hmmim][Tf$_2$N]), 1-hexyl-3-methylimidazolium trifluoromethanesulfonate ([hmim][TfO]), and combinations thereof.

12. The method of claim 1, wherein the method provides an olefin/non-olefin selectivity of at least about 6 or at least about 7 at 35° C.

13. The method of claim 1, wherein the porous support comprises aluminum oxide.

* * * * *